United States Patent [19]
Bennett et al.

[11] Patent Number: 5,483,982
[45] Date of Patent: Jan. 16, 1996

[54] DENTAL FLOSS DEVICE

[75] Inventors: Clayton Bennett; Alan Sullivan; Paul Sullivan, all of Dublin, Ireland

[73] Assignee: Forfas, Dublin, Ireland

[21] Appl. No.: 204,350

[22] PCT Filed: Sep. 11, 1992

[86] PCT No.: PCT/IE92/00007

§ 371 Date: Mar. 11, 1994

§ 102(e) Date: Mar. 11, 1994

[87] PCT Pub. No.: WO93/04641

PCT Pub. Date: Mar. 18, 1993

[30] Foreign Application Priority Data

Sep. 11, 1991 [IE] Ireland .................................. 2311/91
Feb. 7, 1992 [IE] Ireland .................................. 920.410

[51] Int. Cl.⁶ ............................................. A61C 15/00
[52] U.S. Cl. ............................................. 132/323
[58] Field of Search ............................. 132/323, 324, 132/326, 327

[56] References Cited

U.S. PATENT DOCUMENTS

| | | | |
|---|---|---|---|
| 2,187,899 | 1/1940 | Henne | 132/323 |
| 3,892,249 | 7/1975 | Jones et al. | 132/323 |
| 3,927,686 | 12/1975 | Zambito | 132/323 |
| 4,051,857 | 10/1977 | Zambito | 132/323 |
| 4,192,330 | 3/1980 | Johnson | 132/323 |
| 4,942,892 | 7/1990 | Lai | 132/323 |
| 5,056,540 | 10/1991 | Page | 132/323 |
| 5,125,424 | 6/1992 | Eisen | 132/323 |
| 5,170,809 | 12/1992 | Imai et al. | 132/323 |
| 5,261,430 | 11/1993 | Mochel | 132/323 |

*Primary Examiner*—Cary E. O'Connor
*Attorney, Agent, or Firm*—Jacobson, Price, Holman & Stern

[57] ABSTRACT

A dental floss device (1, 40, 50, 60, 70) comprises a handle (2) having a shank (3) terminating in a head piece (4). A disposable dental floss holder (5) comprises a base portion (10) and a pair of spaced-apart jaws (11, 12) with a length of dental floss (13) extending therebetween. The head piece (4) has a groove (20) in which the base portion (10) is securely retained when the device is used in all flossing directions. Snap-fit projections (15) extend inwardly from the jaws (11, 12) of the floss holder (5) and are retained behind marginal edges (25) of a floor (24) of the groove (20). When used, the floss holder (5) is removed and a new floss holder (5) is fitted.

17 Claims, 7 Drawing Sheets

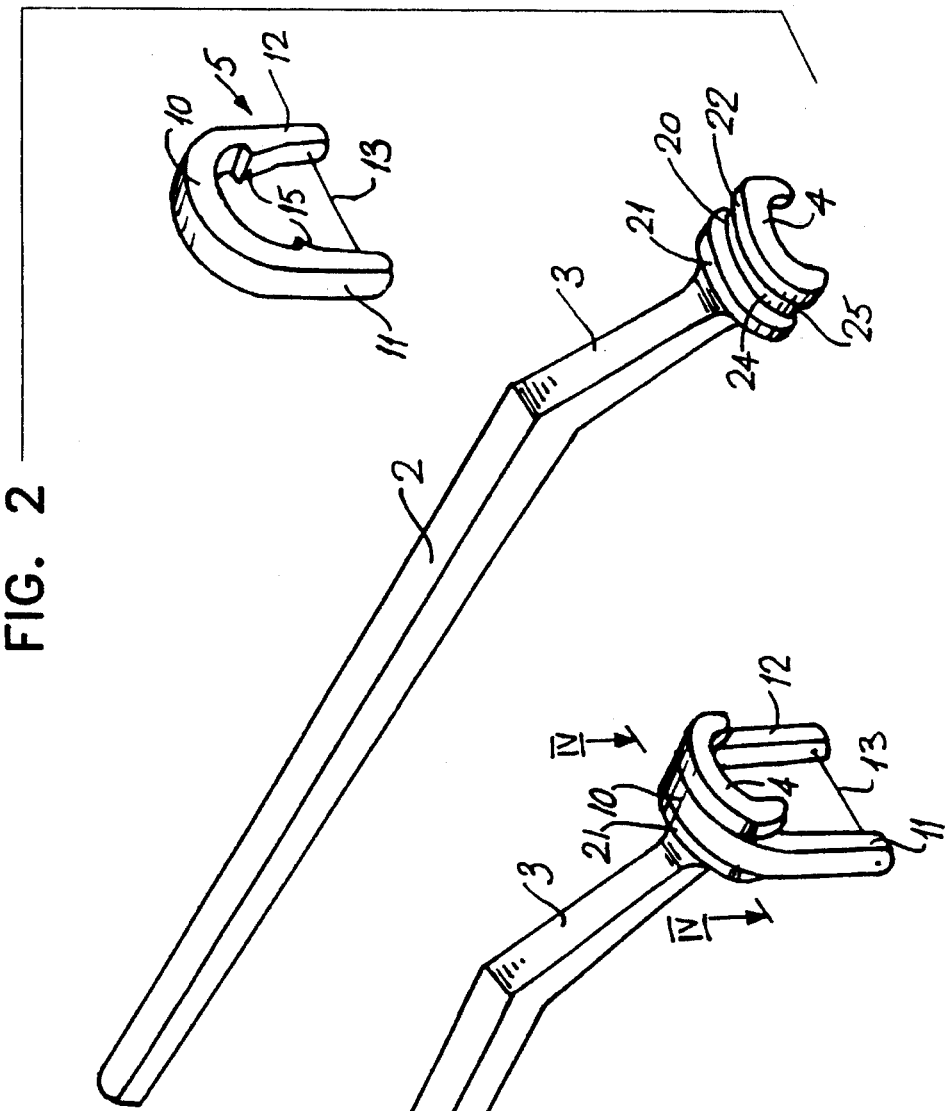
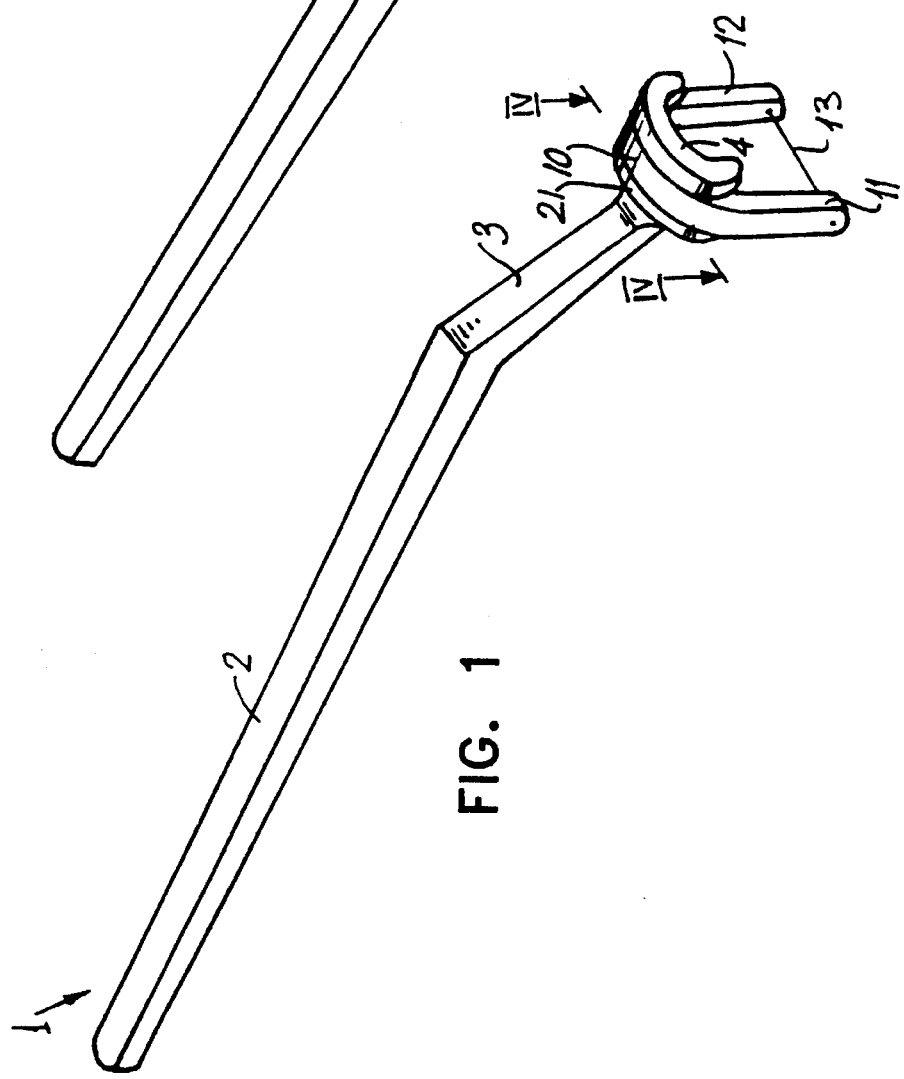

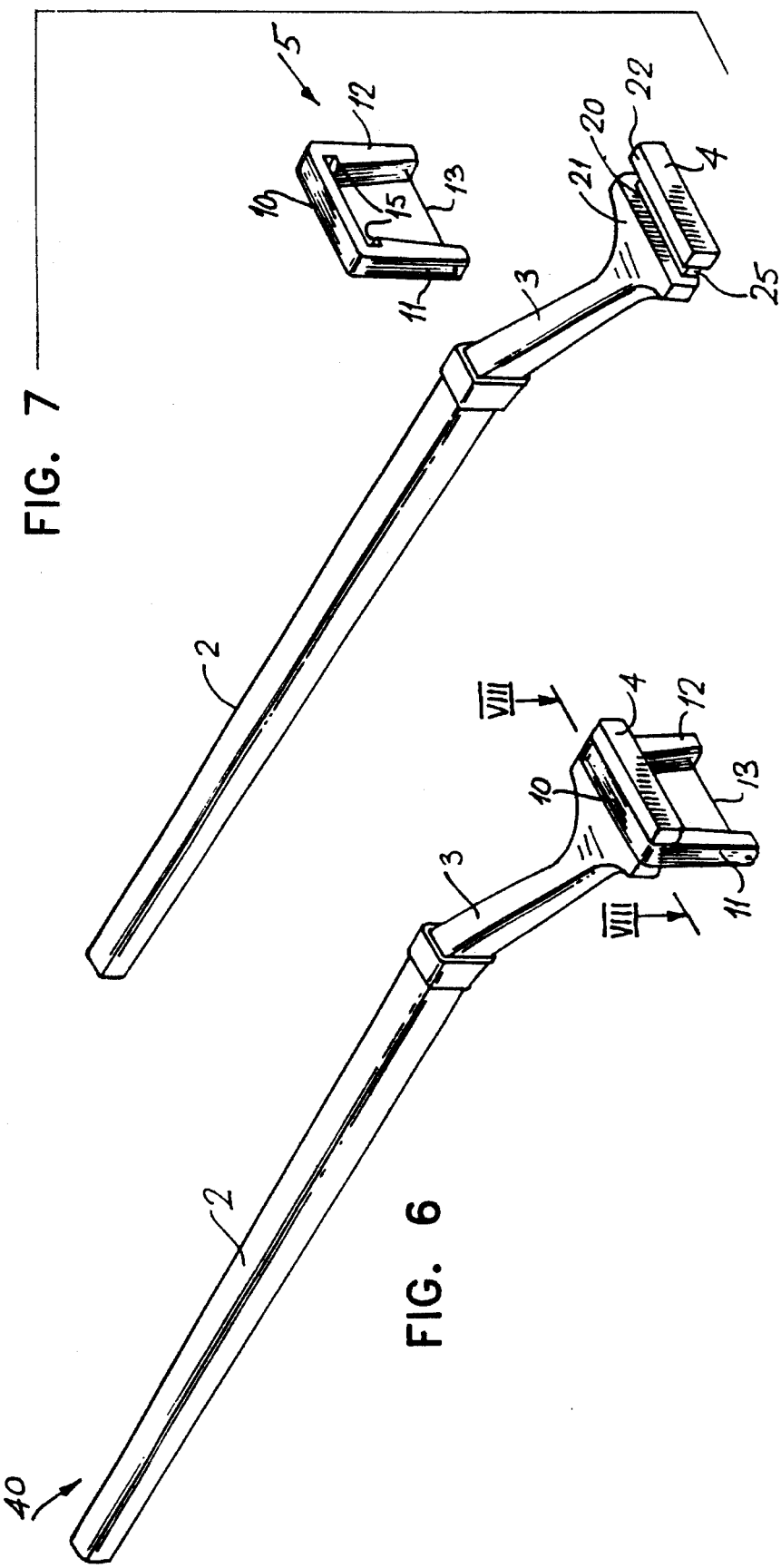

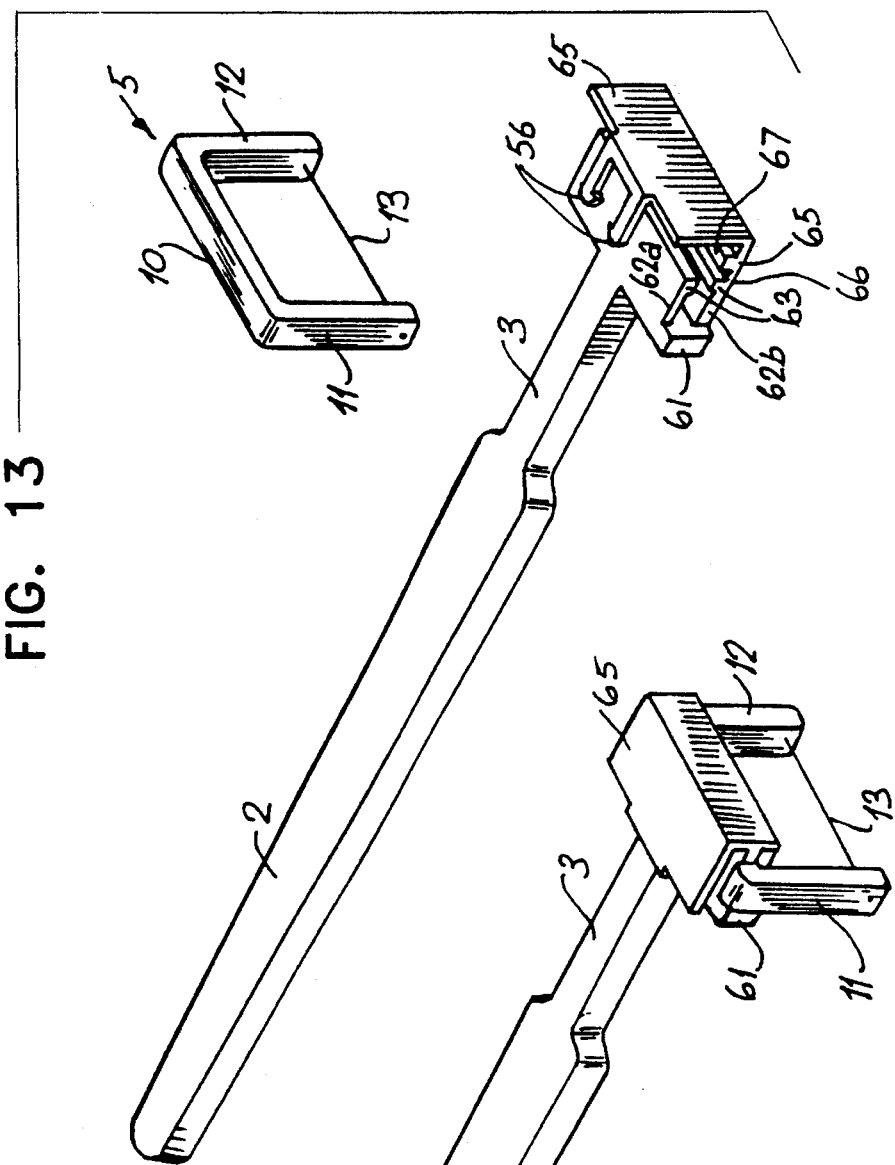
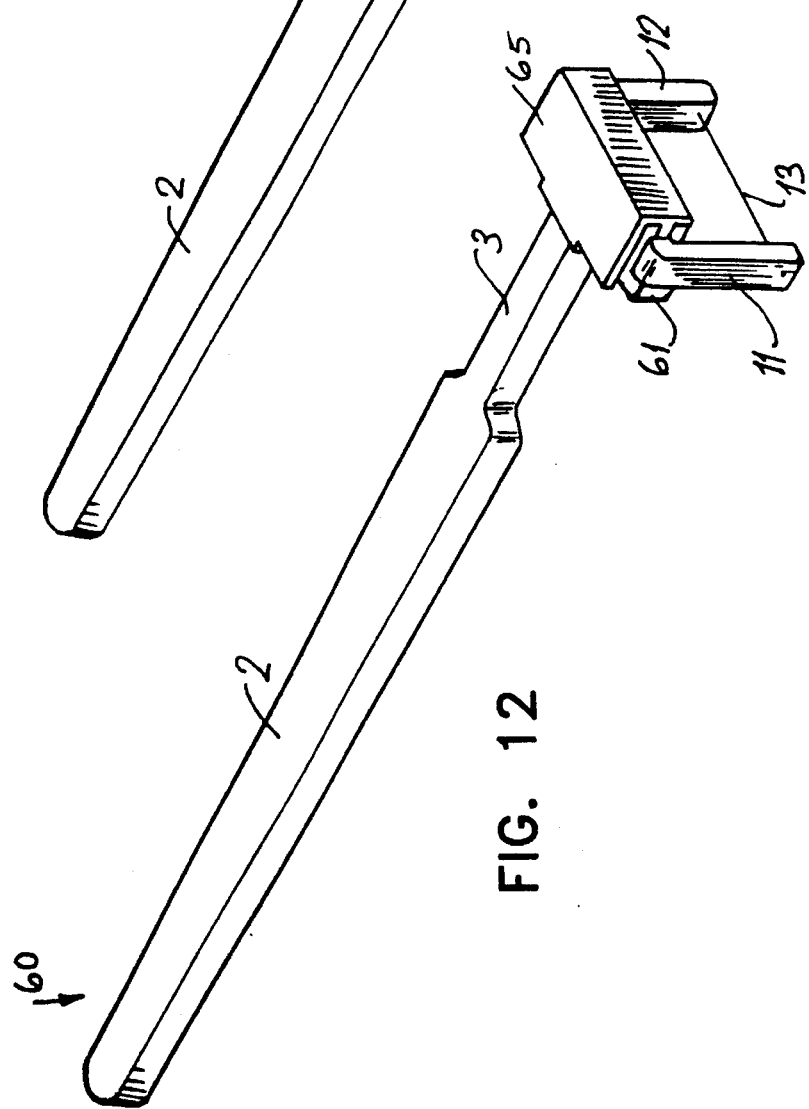

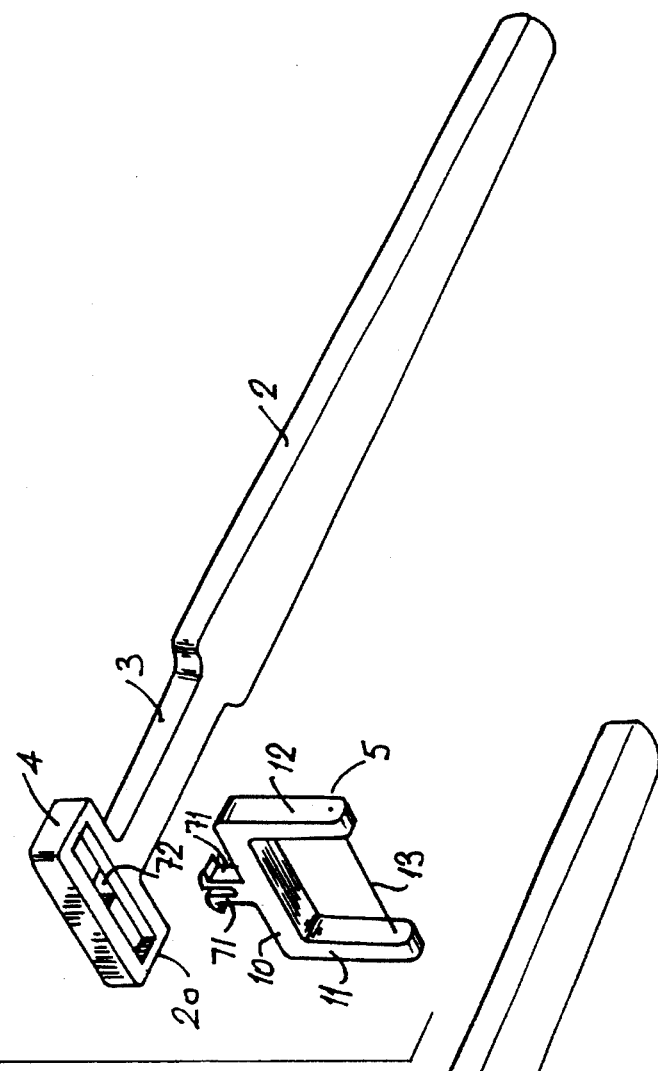

DENTAL FLOSS DEVICE

The invention relates to a dental floss device of the type comprising a handle having a head piece, a disposable dental floss holder and releasable engagement means between the head piece and holder for fitting and disposal of the holder.

A dental floss device of this type is described in U.S. Pat. No. 3,892,249. The device described in this prior specification comprises a handle having a curved head piece with in-turned Jaws which have formations which interengage with complementary formations on a dental floss holder. The holder is of flexible material and is bowed for fitting to the Jaws of the head piece and thumb pressure applied.

One of the problems with known dental floss devices of this type is that the dental floss holder may be difficult to engage and disengage with the head piece. There is also a substantial risk of the dental floss holder becoming detached from the head piece in use in the mouth.

This invention is directed towards providing a dental floss device which will overcome at least some of the problems with known devices.

This invention is characterised in that the releasable engagement means on the head piece and holder is arranged to retain the holder securely in position on the head piece during movement of the holder in use in the mesio-distal, bucco-lingual and gingivo-incisal directions.

The advantage of this arrangement is in ensuring that the device may be effectively and safely used in all directions of operation in use. The distal-medial direction refers to the direction across the face of a tooth in a substantially horizontal plane. The bucco-lingual direction refers to the movement interproximally in a substantially horizontal plane. The gingivo-incisal motion refers to the flossing motion in a vertical plane.

In one embodiment of the invention the holder comprises a base portion and a pair of spaced-apart Jaws extending from the base portion to accommodate a length of dental floss therebetween and the releasable engagement means includes engagement means between the base of the head piece and the holder. This arrangement facilitates the flossing action in use and ease of manufacture.

The length of floss may be integral with the Jaws or may be attached thereto by any suitable means such as adhesives or the like.

In a preferred embodiment of the invention the releasable engagement means includes a transversely extending groove on the holder or head piece and a complementary tongue portion on the other of the holder or head piece which interengage an assembly.

The provision of a transverse groove and tongue affords particular advantages of strength in use and ease of attachment and disconnection of the holder.

Preferably the releasable engagement means includes snap-fitting means between the holder and head piece. Snap-fitting engagement in addition to the tongue and groove arrangement provides for ease of attachment and disconnection while adding to the ability of the connection to resist the forces generated in use.

In one case the snap-fitting means comprises snap-fit projection(s) on one of the holder or head piece which engage with corresponding recess(es) on the other of the head piece or holder. Preferably for ease of fitting and construction the snap-fit projections and corresponding recesses are provided on the Jaws of the holder and adjacent to the groove of the head piece. Typically the projections extend inwardly from the jaws of the holder to engage with corresponding recesses provided adjacent to the groove of the head piece.

In a particularly preferred embodiment which is preferred for ease of fitting and strength in use the groove is of arcuate shape in longitudinal cross section for interengagement with a correspondingly shaped tongue portion.

In another embodiment of the invention the snap-fit projections extend from one of the holder or head piece to engage a complementary recess in the other of the holder or head piece. Typically there are two spaced-apart and oppositely directed snap-fit projections for engagement with a recess provided by a slot. In one case for easeof construction and use the slot is provided in the holder and the snap projections extend from the head piece to snap-fittingly engage in the slot.

According to a further embodiment of the invention the head piece includes an additional retaining means for movement between a released position for fitting and removal of the head piece to a locking position substantially enclosing the head piece in the holder. This arrangement leads to a particularly strong construction.

For ease of construction and use the additional retaining means may be hingedly connected, for example, by means of a live hinge, to the head piece.

For additional strength and ease of use the additional retaining means snap-fittingly engages, typically by snap-fit projections on the additional retaining means, with the head piece in the locking position.

In another embodiment of the invention the releasable engagement means comprises a spigot extending from the head piece of the holder to engage with a complementary socket in the other of the holder or head piece.

In a particularly preferred arrangement the socket is provided in the head piece and the spigot extends from the holder to engage the socket.

Preferably the handle includes a shank portion which is inclined in the longitudinal direction at an angle of between 145° and 180° to the handle.

Preferably also the handle includes a shank portion and the head-piece is inclined in the longitudinal direction at an angle of between 125° and 180° to the neck portion.

The device is most preferably substantially of plastics material. The head piece may be of the same or different plastics material than that of the holder.

The invention will be more clearly understood from the following description thereof given by way of example only with reference to the accompanying drawings in which:

FIG. 1 is a perspective view of a dental floss device according to one embodiment of the invention;

FIG. 2 is an exploded view of the dental floss device of FIG. 1;

FIG. 6 is a perspective view of another dental device according to the invention;

FIG. 7 is an exploded view of the device of FIG. 6;

FIG. 12 is a perspective view of another dental floss device according to the invention;

FIG. 13 is an exploded view of the device of FIG. 12;

FIG. 15 is a perspective view of a further dental floss device according to the invention;

FIG. 16 is an exploded view of the dental floss device of FIG. 15; and

Figure 3:
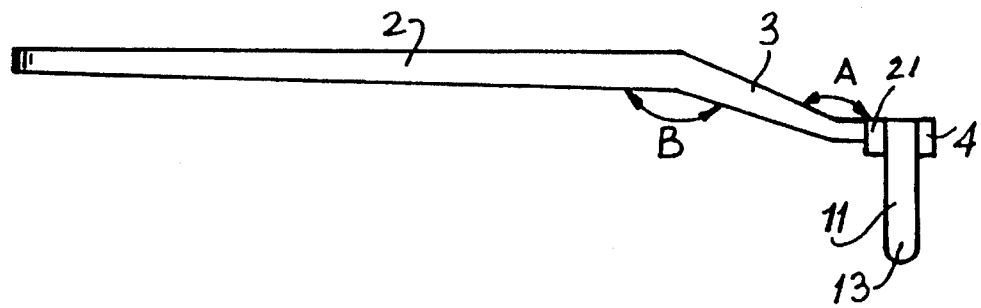
FIG. 3 is a side view of the device.

Referring to the drawings and initially to FIGS. 1 to 5 thereof there is illustrated a dental floss device according to the invention indicated generally by the reference numeral 1. The device 1 comprises a handle 2 having a shank portion 3 terminating in a head piece 4. The dental floss device 1 also comprises a disposable dental floss holder 5, the holder 5 and the head piece 4 having releasable engagement means for fitting and disposal of the holder 5.

The holder 5 comprises a base portion 10 which in this case is of arcuate shape in longitudinal cross section and a pair of spaced-apart Jaws 11, 12 extending from the base portion 10 to accommodate a length of dental floss 13 therebetween. The dental floss 13 may be integrally moulded with the holder 5 or may-be attached by any suitable means to the holder such as by adhesive bonding.

Figure 4:
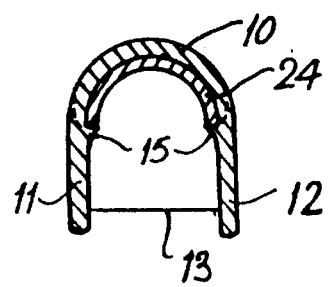
FIG. 4 is a cross-sectional view of the device.

The releasable engagement means in this case include snap-fit projections 15 which extend inwardly from the Jaws 11, 12 of the holder 5 as will be particularly apparent from FIGS. 4 and 2.

The head piece 4 of the handle 2 includes a transversely extending groove 20 defined between a pair of upstanding shoulders 21, 22 and a floor 24 of the head piece 4. The groove 20 is of similar shape and dimension to that of the base portion 10 of the holder 5 and the marginal edges 25 of the floor 24 of the groove 20 are rounded to accommodate the snap-fit projections 15 as they ride over the marginal edges 25 of the floor 24 of the groove. At least part of the base portion 10 of the floss holder 4 defines a tongue portion which in use is securely retained within the groove 20.

In use, the holder 5 is fitted to the head piece by first inserting the head piece 4 through the gap defined between the jaws 11, 12 of the holder 5 and dropping the holder 5 into the groove 20. Light finger pressure is then applied to the base 10 of the holder 5 to push the snap-projections 15 over the marginal edges 25 of the groove 20 until they engage with the floor 24 of the groove 20 as illustrated in FIG. 4. In this fitted position the holder 5 is positively restrained from movement or deflection in all positions and directions of use of the dental floss device 1.

Figure 5:
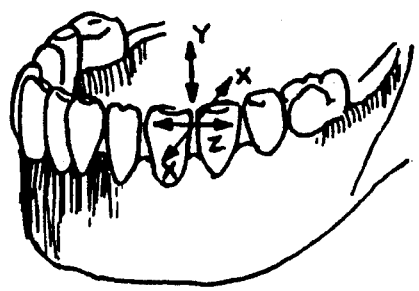
FIG. 5 is a diagrammatic view illustrating the operation of the device.

Referring particulary to FIG. 5 the various directions of use of the dental floss device are diagrammatically illustrated. The arrows X indicate the bucco-lingual direction in which the floss 13 is drawn interproximally forward and backwards in the gap between adjacent teeth. The arrows Z indicate the mesio-distal direction which is the movement of the floss across the face of the teeth. The arrows Y indicate the gingivo-incisal directions of the cleaning action in a vertical plane Z using the dental floss device.

Referring particulary to FIG. 3 it will be appreciated that the handle of the device may be arranged at any suitable angle and may be of any desired shape. For ease of access in use in this case the shank 3 extends at an angle B to the handle 2 of between 145° and 180°. The head piece 4 is inclined at an angle A to the shank 3 of between 125° and 180°. The particular angle and configuration presents a dental floss device which may be readily used with all teeth in the mouth with minimum discomfort to the user. It will be appreciated that in the other embodiments described below similar angular configurations may be utilised.

The invention provides a dental floss device which is of simple construction and easy to use. It offers a dental device with holders for dental floss which can be readily fixed in position and replaced as desired. Because of this simplicity and ease of construction it is anticipated that the device will lead to far more widespread use of dental floss. Because the dental floss holder is easily replaceable and yet retained effectively in position in all directions of use it is easy and safe to use.

Figure 8:
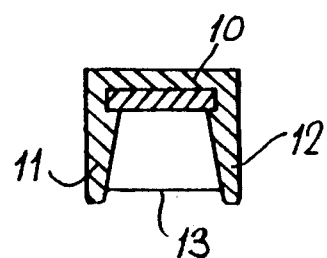
FIG. 8 is a cross-sectional view of the device of FIG. 6.

Referring to FIGS. 6 to 8 there is illustrated another dental floss device according to the invention indicated generally by the reference numeral 40. The device 40 is similar to the device described above with reference to FIGS. 1 to 4 and like parts are assigned the same reference numerals. In this case the base portion 10 of the dental floss holder 5 and the groove 20 of the head piece 4 are of generally horizontal rather than arcuate shape in longitudinal cross section. It is anticipated that this device according to this embodiment of the invention will be slightly cheaper due to less complex moulding requirements.

Figure 10:
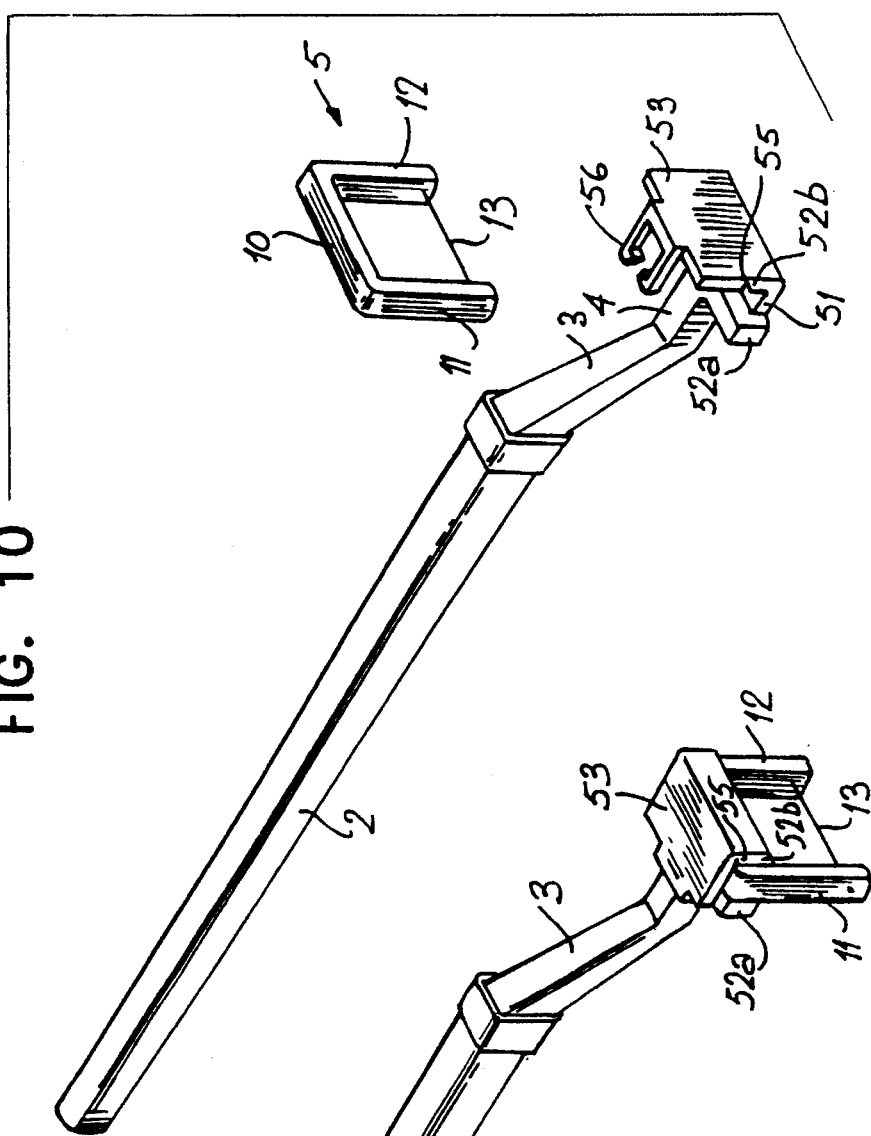
FIG. 10 is an exploded view of the device of FIG. 9.
Figure 9:
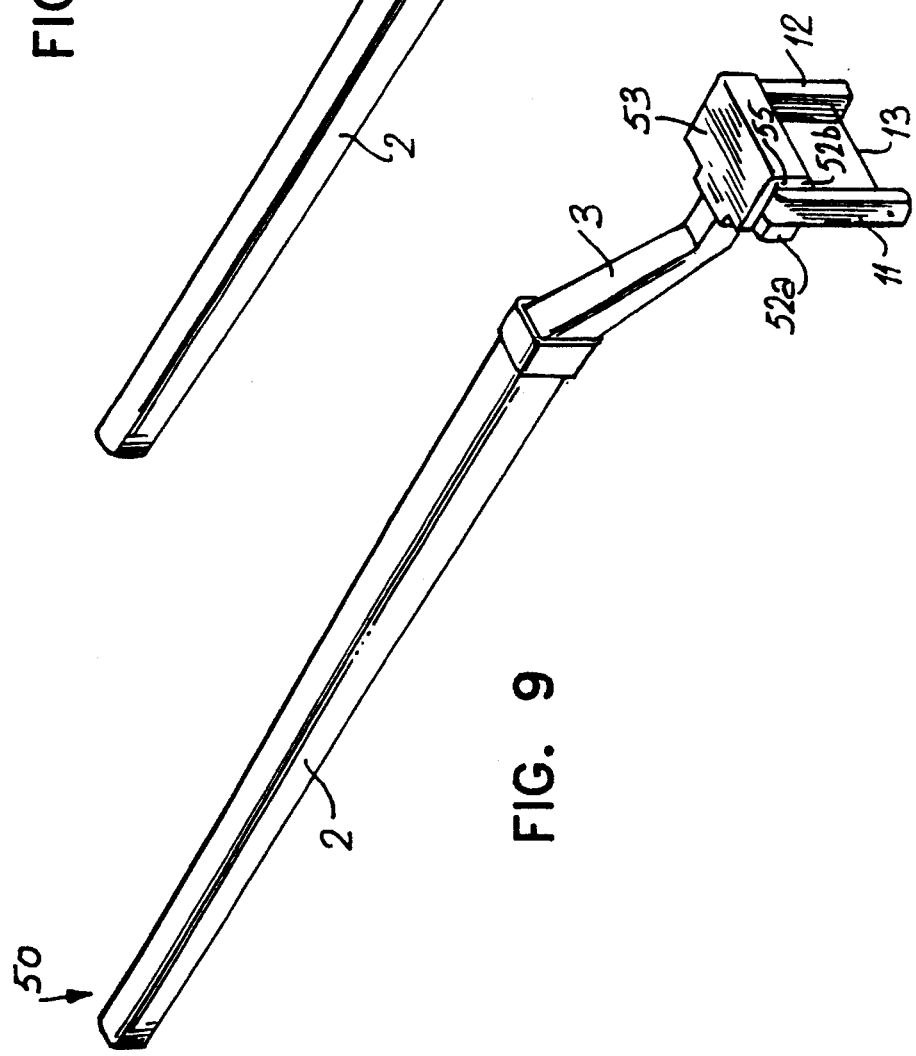
FIG. 9 is a perspective view of another dental floss device according to the invention.
Figure 11:
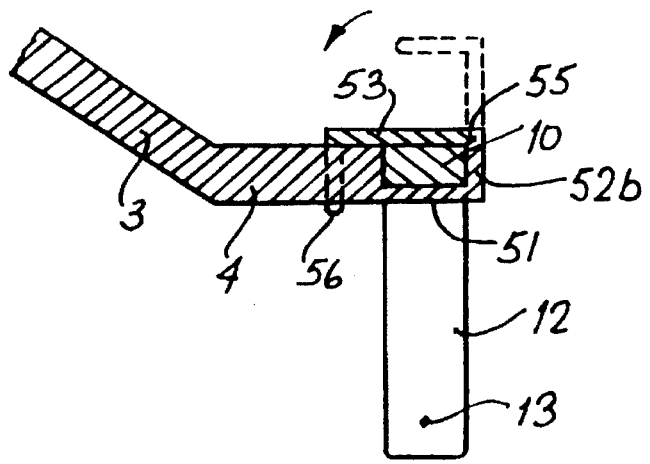
FIG. 11 is a partial side cross-sectional view of the device of FIG. 9.

Referring to FIGS. 9 to 11 there is illustrated another dental floss device 50 according to the invention. The device 50 is again similar to the device illustrated in FIGS. 1 to 5 and like parts are assigned the same reference numerals. In this case the head piece comprises a channel member having a base 51, a first side web 52a extending from the shank 3 and a second side web 52b which are sized and shaped to receive the base portion 10 of the dental floss holder 5. Additional retaining means 4 for retaining the holder in position is in this case provided by an extension plate 53 which extends from and is hingedly interconnected by a plastics hinge 55 to the side web 52b. The extension plate 53 has inwardly extending snap-fit projections 56 which engage over the shank 3 of the handle when the plate member 53 is hinged into the closed or locked position illustrated in FIGS. 9 and 11. In the locked position illustrated in FIGS. 9 and 11 it will be noted that the base portion 10 of the dental floss holder 5 is completely confined against movement in all directions in use leading to a particularly strong construction. It will be noted that the side web 52a is extended sidewardly to provide a shoulder to engage part of the jaws 11, 12 of the holder 5 to assist in retaining the holder securely in position. To replace the floss holder 5 the snap projections 56 are released from the shank 3 of the handle and the extension plate 53 is pushed into the release position illustrated in FIG. 11 allowing the holder 5 to be removed and a fresh holder to be placed in position. For ease of fitting and removal of a holder 5 from the device the hinge 55 may be a live hinge which biases the snap projections 56 towards the shank 3 and/or away from the shank 3 to facilitate insertion and removal of a floss holder 5.

Figure 14:
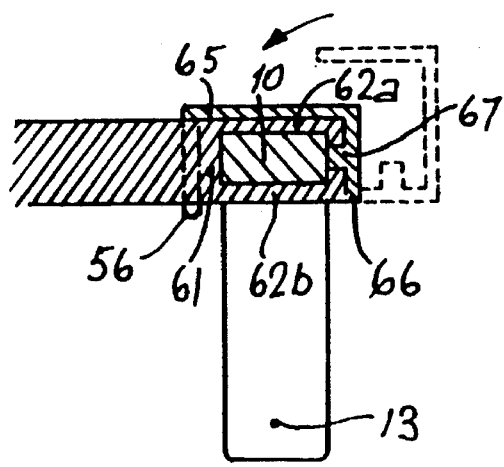
FIG. 14 is a partial side cross-sectional view of the device of FIG. 12.

Referring to FIGS. 12 to 14 there is illustrated another dental floss holder according to the invention indicated generally by the reference numeral 60. The dental floss holder 60 is similar to the holder illustrated in FIGS. 7 to 9 and like parts are assigned the same reference numerals. In this case the groove 20 in the head piece 4 for receiving the floss holder 5 is defined by a base wall 61 and side webs 62a, 62b projecting from the base wall 61, the side webs having in-turned edges 63 to facilitate snap-in of the holder in the head piece. One of the side webs 62 includes a generally L-shaped extension 65 which is hingedly connected to the web 62b by a plastics hinge 66 and has an inwardly extending projection 67 which, in the locked position illustrated in FIGS. 10 and 12, enters the gap between the projections 63 to even more positively retain the holder 5 in position on the head piece 4. The device is operated in a similar manner to the device illustrated in FIGS. 9 to 11.

Figure 17:
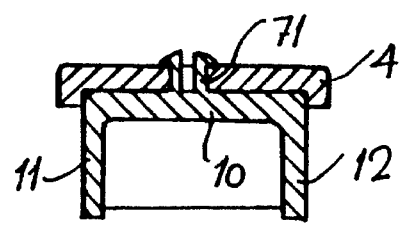
FIG. 17 is a cross-sectional view of the device of FIG. 15.

Referring to FIGS. 15 and 17 there is illustrated another dental floss device according to the invention indicated generally by the reference numeral 70 which is similar to the device described above with reference to FIGS. 1 to 5 and like parts are assigned the same reference numerals. In this case the releasable engagement means between the floss holder 5 and head piece 4 comprises a pair of snap-fit projections 71 extending from the base portion 10 of the holder 5 to engage in a complementary socket 72 in the head piece 4. To release the holder 5 a user draws the snap-projections 71 towards each other allowing the projections to move freely through the socket 72. It will be noted that in this case the groove 20 is closed at both ends to securely retain the holder 5 in position in the head piece 4.

An additional retaining means may be provided for retaining the snap projections 71 splayed in the locked position. The additional retaining means may comprise a spike-like member for insertion between the projections 71. The spike-like member may be attached to the head piece 4 by a hinge arrangement.

The dental floss device may be of any suitable material of construction. Preferably the device is of substantially plastics material. The head piece may be of the same or different plastics material than that of the holder.

Many variations on the embodiments of the invention described will be readily apparent and accordingly the invention is not limited to the embodiments hereinbefore described which may be varied in both construction and detail.

We claim:

1. A dental floss device comprising:

a handle having a head piece;

a disposable dental floss holder for interengagement with the head piece, on assembly;

the dental floss holder comprising a base portion and a pair of spaced-apart jaws extending from the base portion to accommodate a length of dental floss therebetween; and releasable engagement means between the head piece of the handle and the dental floss holder for retaining the dental floss holder securely in position on the head piece of the handle during movement of the dental floss device, in use;

the head piece of the handle or the base portion of the dental floss holder defining a transversely extending groove, and the other of the base portion of the dental floss holder or head piece of the handle having a complementary tongue portion which engages the transversely extending groove, on assembly, the tongue portion and transversely extending groove defining part of the releasable engagement means, the releasable engagement means also including snap-fitting means between the dental floss holder and the head piece of the handle, the jaws of the dental floss holder or the head piece having snap-fit projections and the other of the jaws of the dental floss holder or head piece defining corresponding recesses which together with the snap-fit projections constitute said snap-fitting means, the snap-fit projections engaging with the recesses upon engagement of the tongue portion with the transversely extending groove.

2. The dental floss device as claimed in claim 1 wherein handle includes a shank portion which is inclined in the longitudinal direction at an angle of between 145° and 180° to the handle.

3. The dental floss device as claimed in claim 1 wherein the handle includes a shank portion and the head-piece is inclined in the longitudinal direction at an angle of between 125° and 180° to the shank portion.

4. The dental floss device as claimed in claim 1 wherein the device is substantially of plastics material.

5. The dental floss device as claimed in claim 4 wherein the head piece is of the same plastics material as that of the disposable dental floss holder.

6. The dental floss device as claimed in claim 4 wherein at least a portion of the disposable dental floss holder is of a different plastics material than that of the head piece.

7. The dental floss device of claim 1, wherein the groove is of arcuate shape in longitudinal cross section for interengagement with said tongue portion, said tongue portion having a correspondingly arcuate shape.

8. The dental floss device of claim 1, wherein said groove is defined by the head piece of the handle, and the tongue portion is defined by the base portion of the dental floss holder.

9. The dental floss device of claim 8, wherein the snap-fit projections extend inwardly from the jaws of the dental floss holder to engage with said recesses, said recesses being provided in said head piece adjacent to the groove.

10. The dental floss device of claim 1, wherein the head piece includes an additional retaining means for movement between a released position for fitting and removal of the head piece, and a locking position substantially closing said head piece around the disposable dental floss holder.

11. The dental floss device of claim 10, wherein said additional retaining means is hingedly connected to the head piece.

12. The dental floss device of claim 11, wherein said additional retaining means is hingedly connected to the head piece by a live hinge.

13. The dental floss device of claim 10, wherein said additional retaining means snap-fittingly engages with the head piece in the locking position.

14. The dental floss device of claim 13, wherein the additional retaining means is provided with snap-fit projections which engage with the head piece in the locking position.

15. A dental floss device comprising:

a handle having a head piece;

a disposable dental floss holder, and releasable engagement means between the head piece and the disposable dental floss holder for fitting and disposal of the disposable dental floss holder said releasable engagement means being arranged to retain the disposable dental floss holder securely in position on the head piece during movement of the holder in use in the mesio-distal, bucco-lingual and gingivo-incisal directions, wherein the releasable engagement means includes a transversely extending groove on the disposable dental floss holder or head piece and a complementary tongue portion on the other of the disposable dental floss holder or head piece which interengage on assembly transversely extending groove being closed at both ends to securely retain the tongue portion, and wherein snap-fit projections extend from one of the disposable dental floss holder or head piece to engage a complementary recess in the other of the disposable dental floss holder or head piece.

16. A dental floss device comprising:

a handle having a head piece, a disposable dental floss holder, and releasable engagement means between the head piece and the disposable dental floss holder for fitting and disposal of the disposable dental floss holder, said releasable engagement means being arranged to retain the disposable dental floss holder securely in position on the head piece during movement of the holder in use in the mesio-distal, bucco-lingual and gingivo-incisal directions, wherein the head piece includes an additional retaining means for movement between a released position for fitting and removal of the head piece and a locked position substantially closing the head piece around the disposable dental floss holder, wherein the additional retaining means is hingedly connected to the head piece by a live hinge.

17. A dental floss device comprising:

a handle having a head piece, a disposable dental floss holder, and releasable engagement means between the head piece and the disposable dental floss holder for fitting and disposal of the disposable dental floss holder, said releasable engagement means being arranged to retain the disposable dental floss holder securely in position on the head piece during movement of the holder in use in the mesio-distal, bucco-lingual and gingivo-incisal directions, wherein the head piece includes an additional retaining means for movement between a released position for fitting and removal of the head piece and a locked position substantially closing the head piece around the disposable dental floss holder, wherein the additional retaining means is provided with snap-fit projections which engage with the head piece in the locking position to thereby snap-fittingly engage the additional retaining means to the head piece.

* * * * *